United States Patent
Altmann et al.

(10) Patent No.: US 12,349,962 B2
(45) Date of Patent: Jul. 8, 2025

(54) SEQUENTIAL ACTIVATION OF ELECTRODE-PAIRS DURING IRREVERSIBLE ELECTROPORATION (IRE)

(71) Applicant: BIOSENSE WEBSTER (ISRAEL) LTD., Yokneam (IL)

(72) Inventors: Andres Claudio Altmann, Haifa (IL); Assaf Govari, Haifa (IL); Ella Ozeri, Binyamina (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 784 days.

(21) Appl. No.: 16/926,937

(22) Filed: Jul. 13, 2020

(65) Prior Publication Data
US 2022/0008123 A1 Jan. 13, 2022

(51) Int. Cl.
*A61B 18/00* (2006.01)
*A61B 18/12* (2006.01)
*A61B 18/14* (2006.01)

(52) U.S. Cl.
CPC ...... *A61B 18/1492* (2013.01); *A61B 18/1206* (2013.01); *A61B 2018/00375* (2013.01); *A61B 2018/00577* (2013.01); *A61B 2018/00613* (2013.01); *A61B 2018/126* (2013.01); *A61B 2018/1467* (2013.01)

(58) Field of Classification Search
CPC ...... A61B 18/1492; A61B 2018/00613; A61B 2018/126; A61B 2018/1467
See application file for complete search history.

(56) References Cited

U.S. PATENT DOCUMENTS

| | | |
|---|---|---|
| 5,391,199 A | 2/1995 | Ben |
| 6,239,724 B1 | 5/2001 | Doron |
| 6,332,089 B1 | 12/2001 | Acker |
| 6,484,118 B1 | 11/2002 | Govari |
| 6,618,612 B1 | 9/2003 | Acker |
| 6,690,963 B2 | 2/2004 | Ben |
| 7,756,576 B2 | 7/2010 | Levin |
| 7,848,787 B2 | 12/2010 | Osadchy |
| 7,869,865 B2 | 1/2011 | Govari |
| 8,048,067 B2 | 11/2011 | Davalos |
| 8,221,411 B2 | 7/2012 | Francischelli |
| 8,456,182 B2 | 6/2013 | Bar-Tal |

(Continued)

FOREIGN PATENT DOCUMENTS

| | | |
|---|---|---|
| CN | 111248994 A | 6/2020 |
| WO | WO1996005768 A1 | 2/1996 |
| WO | WO2021113463 A1 | 6/2021 |

OTHER PUBLICATIONS

European Search Report for corresponding EPA No. 21165817.4 dated Sep. 30, 2021.

*Primary Examiner* — Jaymi E Della
(74) *Attorney, Agent, or Firm* — Dergosits & Noah LLP; Todd A. Noah

(57) ABSTRACT

An irreversible electroporation (IRE) method includes placing multiple electrodes of a catheter in contact with tissue of an organ. Bipolar IRE pulses are generated. The tissue is ablated by applying the bipolar IRE pulses to pairs of the electrodes, in accordance with an order in which successive activations of a given electrode-pair are interleaved with activation of at least one other electrode-pair, and are spaced in time by at least a predefined duration.

9 Claims, 3 Drawing Sheets

(56) References Cited

U.S. PATENT DOCUMENTS

| | | |
|---|---|---|
| 9,987,081 B1 | 6/2018 | Altmann |
| 10,271,893 B2 | 4/2019 | Stewart |
| 10,342,598 B2 | 7/2019 | Long |
| 10,531,914 B2 | 1/2020 | Stewart |
| 2002/0065455 A1 | 5/2002 | Ben |
| 2003/0120150 A1 | 6/2003 | Govari |
| 2004/0068178 A1 | 4/2004 | Govari |
| 2016/0051324 A1 | 2/2016 | Stewart |
| 2016/0113709 A1 | 4/2016 | Maor |
| 2017/0189097 A1* | 7/2017 | Viswanathan ....... A61N 1/0587 |
| 2018/0085160 A1* | 3/2018 | Viswanathan ......... A61N 1/371 |
| 2018/0214202 A1 | 8/2018 | Howard |
| 2019/0038171 A1* | 2/2019 | Howard ............... A61B 5/7275 |
| 2019/0336207 A1* | 11/2019 | Viswanathan ..... A61B 18/1492 |
| 2020/0009378 A1 | 1/2020 | Stewart |

\* cited by examiner

SEQUENTIAL ACTIVATION OF ELECTRODE-PAIRS DURING IRREVERSIBLE ELECTROPORATION (IRE)

FIELD OF THE INVENTION

The present invention relates generally to invasive ablation using electrical signals, and particularly to irreversible electroporation (IRE) of cardiac tissue.

BACKGROUND OF THE INVENTION

Techniques that use a medical probe to perform irreversible electroporation (IRE) of an intra body tissue were previously proposed in the patent literature. For example, U.S. Patent Application Publication No. 2020/0009378 describes a method, system, and device for electroporation. The system may include a medical device with a plurality of electrodes borne on an expandable element and an energy generator in communication with the electrodes. The energy generator may have processing circuitry configured to selectively deliver electroporation energy to at least one of the electrodes. The processing circuitry may determine whether an alert condition is present and, if so, cease the delivery of electroporation energy to one or more electrodes identified as the cause of the alert condition and/or prevent the delivery of electroporation energy to the one or more electrodes identified as the cause of the alert condition. The energy generator may also be configured to deliver electroporation energy in a sequence of a plurality of energy delivery patterns to enhance lesion formation. In an embodiment, bipolar signals are applied using all pairs of the plurality of electrodes simultaneously and, to prevent overheating of certain electrodes in some cases, these electrodes are disconnected from the energy generator.

As another example, U.S. Patent Application Publication No. 2018/0214202 describes methods, systems, and devices for enhancing the efficiency and efficacy of energy delivery and tissue mapping. One system includes a treatment element having a plurality of electrodes and an energy generator that is configured to deliver electric energy pulses to the electrodes in a variety of patterns. For example, electrodes may be arranged in closely spaced pairs. The energy generator may deliver mapping energy to each electrode in each pair individually to map tissue and may deliver ablation energy to the electrodes in each pair together, such that each pair is treated like a single electrode, to deliver ablation energy, such as bipolar ablation energy between adjacent pairs. One system includes at least one concave electrode, the configuration of which concentrates the energy and drives it deeper into the tissue. One system includes neutral electrodes between active electrodes, the energy generator selectively coupling the neutral electrodes to alter the ablation pattern. In an embodiment, to prevent electrode overheating, effective electrode surface is increased by connecting several electrodes together. In another embodiment, overheated electrodes are disconnected to reduce heat.

U.S. Patent Application Publication No. 2016/0113709 describes selective cellular ablation by electroporation, applicable, for example, to bulk tissue in the beating heart. Protocol parameters potentially induce tissue loss without thermal damage. Device and method are potentially applicable for myocardial tissue ablation to treat arrhythmias, obstructive hypertrophy, and/or to generate natural scaffolds for myocardial tissue engineering. In some embodiments of the invention, pulses are delivered alternately to different pairs of electrodes. In some embodiments, the intensity (pulse voltage, frequency, number, and/or duration) of the electroporation protocol is limited by a requirement to avoid localized heating leading to thermal damage. Thus, for example, electroporation potentials are alternately delivered (optionally with differences in potential corresponding to differences in an inter-electrode distance, to maintain a strength of the electroporating electric filed) between electrode-pairs. In such a configuration, each electrode potentially participates in only half of the activated pairings (e.g., used half of the time).

SUMMARY OF THE INVENTION

An embodiment of the present invention that is described hereinafter provides an irreversible electroporation (IRE) method including placing multiple electrodes of a catheter in contact with tissue of an organ. Bipolar IRE pulses are generated. The tissue is ablated by applying the bipolar IRE pulses to pairs of the electrodes, in accordance with an order in which successive activations of a given electrode-pair are interleaved with activation of at least one other electrode-pair, and are spaced in time by at least a predefined duration.

In some embodiments, applying the bipolar IRE pulses includes applying the bipolar IRE pulses between adjacent electrodes.

In some embodiments, applying the bipolar IRE pulses includes applying at least some of the bipolar IRE pulses between non-adjacent electrodes.

In an embodiment, applying the bipolar IRE pulses includes applying at least some of the bipolar IRE pulses between pairs of groups of electrodes.

In another embodiment, the electrode-pairs have the same inter-electrode distance.

In some embodiments, the tissue includes cardiac tissue, and wherein applying the bipolar IRE pulses includes gating the bipolar IRE pulses to synchronize with refractory periods of the cardiac tissue.

There is additionally provided, in accordance with another embodiment of the present invention, an irreversible electroporation (IRE) system, including a catheter, an IRE ablation power source, and a processor. The catheter has multiple electrodes that are configured to be placed in contact with the tissue of an organ. The IRE ablation power source is configured to generate bipolar IRE pulses. The processor is configured to ablate the tissue by applying the bipolar IRE pulses to pairs of the electrodes, in accordance with an order in which successive activations of a given electrode-pair are interleaved with activation of at least one other electrode-pair, and are spaced in time by at least a predefined duration.

In some embodiments, the system further includes a switching assembly that is configured to switch the IRE ablation power source between the electrode-pairs, and the processor is configured to apply the bipolar IRE pulses in accordance with the order by controlling the switching assembly.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
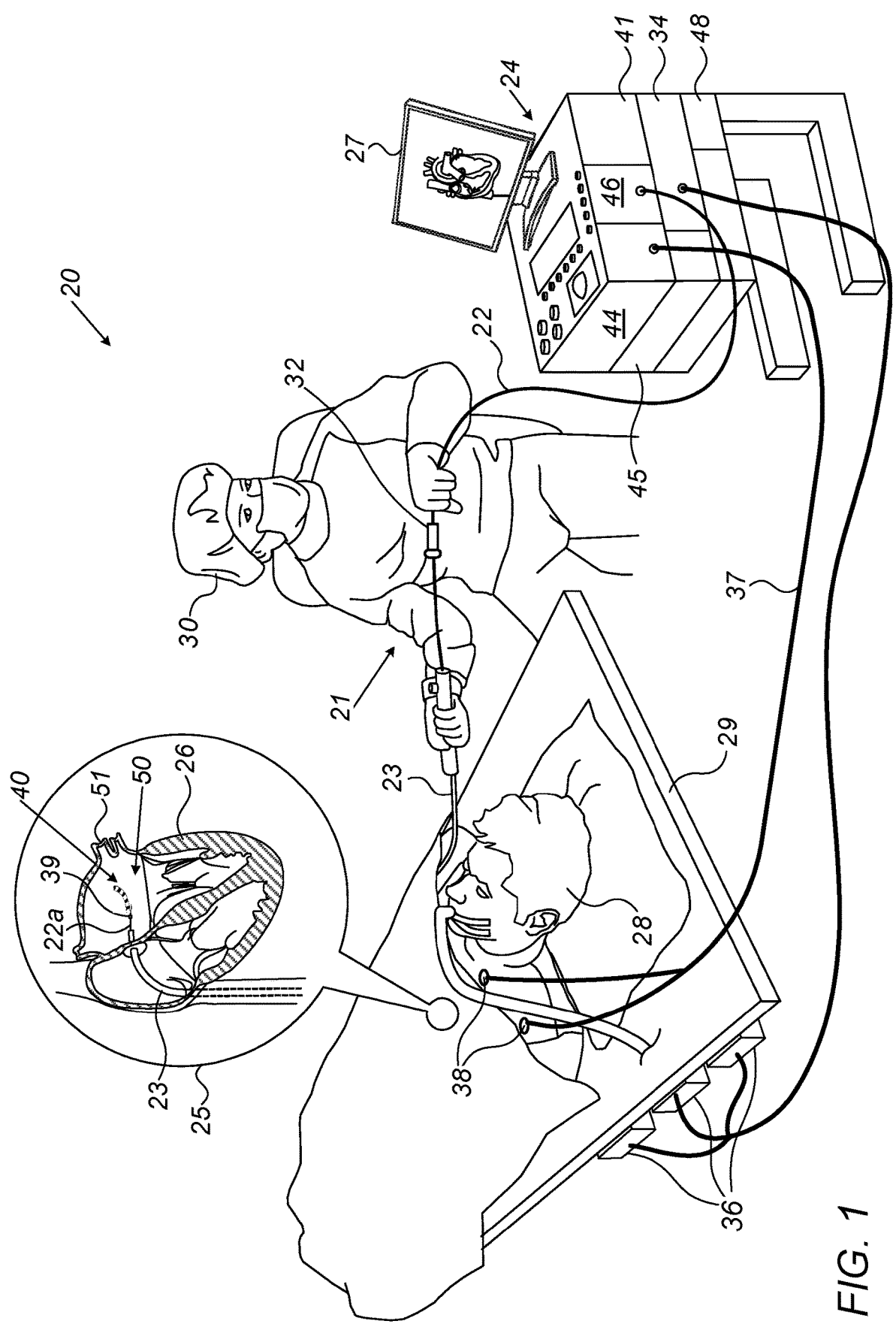
FIG. 1 is a schematic, pictorial illustration of a catheter-based position-tracking and irreversible electroporation (IRE) ablation system, in accordance with an exemplary embodiment of the present invention.

Irreversible electroporation (IRE), also called Pulsed Field Ablation (PFA), may be used as an invasive therapeutic modality to kill tissue cells by subjecting them to high-voltage pulses. Specifically, IRE pulses have a potential use to kill myocardium tissue cells in order to treat cardiac arrhythmia. Cellular destruction occurs when the transmembrane potential exceeds a threshold, leading to cell death and thus the development of a tissue lesion. Therefore, of particular interest is the use of high-voltage bipolar electric pulses (e.g., using a pair of electrodes in contact with tissue) to generate high electric fields (e.g., above a certain threshold) to kill tissue cells between the electrodes.

In the context of this disclosure, "bipolar" voltage pulse means a voltage pulse applied between two electrodes of a catheter (as opposed, for example, to unipolar pulses that are applied by a catheter electrode relative to some common ground electrode not located on the catheter).

To implement IRE ablation over a relatively large tissue region of an organ, such as a circumference of an ostium of a pulmonary vein (PV), it is necessary to use multiple pairs of electrodes of a multi-electrode catheter. To make the generated electric field as spatially uniform as possible over a large tissue region it is best to have pairs of electrodes selected with overlapping fields, or at least fields adjacent to each other. However, there is a Joule heating component that occurs with the IRE generated fields, and this heating may damage the electrodes when multiple pairs of electrodes are continuously used in delivering a sequence of IRE pulses.

The IRE pulse generator is configured to deliver peak power in the range of tens of kW. However, IRE pulses that are intense enough to ablate tissue may also cause unwanted effects of potential clinical hazard. For example, a pulse voltage of 2 kV across 200Ω of tissue (both possible values) momentarily generates a local peak current of 10 A, i.e., 20 kW in the tissue between two electrodes. This voltage, when applied between the electrodes to form a sequence of bipolar IRE pulses, may also be high enough to generate enough Joule heating which, if not quickly dissipated, may generate char.

Embodiments of the present invention that are described hereinafter provide techniques to IRE ablate (i.e., apply the IRE pulses) over a relatively large continuous region of tissue without causing thermal damage to the electrodes and/or to tissue due to electrode overheating. In some embodiments, a system comprising a switching assembly energizes different pairs of electrodes of the multi-electrode catheter, and arranges the timing of the pairs so that no electrode overheats while IRE is applied to tissue, but which still provides continuous spatial ablation. Some embodiments provide a processor-controlled switching box (e.g., a "switching assembly"). During application of IRE ablative power by the electrodes, the processor can, by controlling the switching box, switch between electrode-pairs.

The energizing of the different electrode-pairs (whether they are of adjacent electrodes or non-adjacent electrodes), and the times needed for Joule heating to dissipate, are predetermined in a protocol (e.g., by an algorithm). In particular, no electrode pair is used successively. For example, the protocol may specify applying the bipolar IRE pulses to pairs of the electrodes, in accordance with an order in which successive activations of a given electrode-pair are interleaved. In other words, the activation of at least one other electrode-pair should occur between successive activations of a given electrode-pair. Such a protocol ensures that any two activations of a same electrode-pair are spaced in time (i.e., time gapped) by at least a predefined duration. The time gap may range between 0.2 microsecond to 20 mSec, typically being 5 mSec.

In yet another embodiment, a protocol is optimized to sequentially energize electrode-pairs (i.e., interleave activations) over an entire circumference of a loop head catheter to perform IRE ablation over an entire circumference of a lumen, such as an ostium of a PV.

As used herein, the term "approximately" for any numerical values or ranges indicate a suitable dimensional tolerance that allows the part or collection of components to function for its intended purpose as described herein. More specifically, "approximately" may refer to the range of values±20% of the recited value, e.g. "approximately 90%" may refer to the range of values from 71% to 99%.

In another embodiment, the distance between the electrodes in each pair is the same across all the pairs. By keeping the same inter-electrode distance in each electrode-pair, the processor maintains applying a uniform electric field strength across the lesion as long as the pulses are the same. Inter-electrode distance of an electrode-pair can range from 0.5 mm to 15 mm typically being 3.5 mm.

The disclosed sequential IRE ablation method applies to many types of multi-electrode catheters, including expendable-frame catheters such as balloon or basket catheters. The technique is also applicable to loop catheters, such as the Lasso™ catheter, and to multi-arm catheters such as the PentaRay™ catheter (both made by Biosense Webster, Irvine, California). Catheters of other shapes can also be used with the disclosed technique, such those having deflectable tips disposed with a one-dimensional array of electrodes, or flat catheters disposed with a two-dimensional array of electrodes. The electrodes themselves may have any shape suitable for bipolar IRE ablation, e.g. flat or ring.

Typically, the processor is programmed in software containing a particular algorithm that enables the processor to conduct each of the processor-related steps and functions outlined above.

By sequencing electrode-pair bipolar IRE ablation according to a prespecified protocol (e.g., algorithm), the disclosed sequenced multi-electrode IRE ablation technique can provide safer and more effective IRE ablation treatments.

System Description

FIG. 1 is a schematic, pictorial illustration of a catheter 21 based position-tracking and irreversible electroporation (IRE) ablation system 20, in accordance with an embodiment of the present invention. System 20 comprises a deflectable tip section 40, illustrated in inset 25, that is fitted at a distal end 22a of a shaft 22 of catheter 21 with deflectable tip section 40 comprising multiple electrodes 50 (seen in detail in FIG. 2). In the embodiment described herein, electrodes 50 are used for IRE ablation of tissue of the left atrium of heart 26, such as IRE ablation of an ostium 51 of a pulmonary vein in heart 26.

Figure 3:
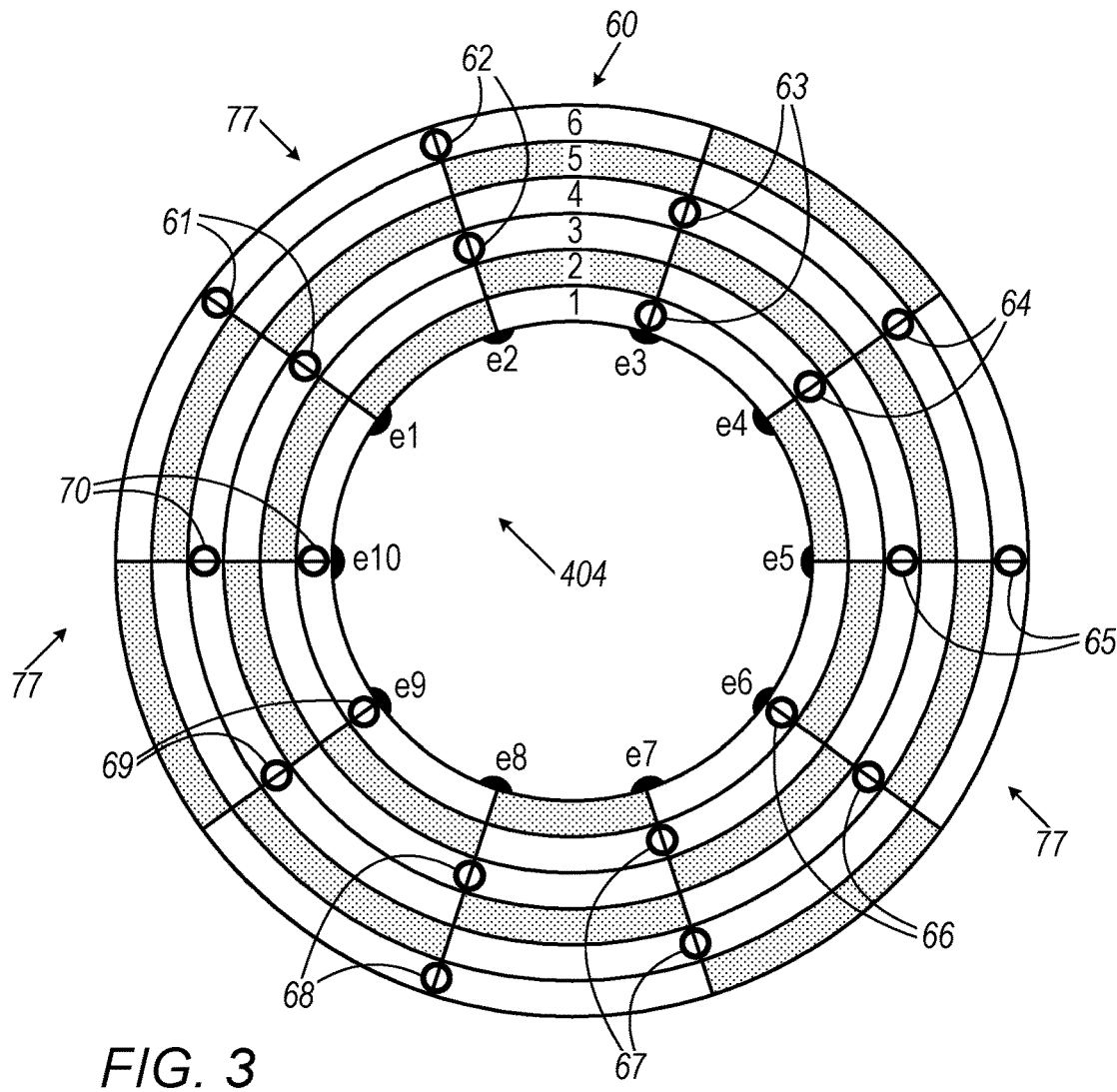
FIG. 3 is a schematic front view of sequenced energization of electrode-pairs of a multi-electrode deflectable tip section of a catheter deployed in a form of a loop, in accordance with an exemplary embodiment of the invention.

The proximal end of catheter 21 is connected to a control console 24 comprising an ablative power source 45. Console 24 includes a switching box 46 (also referred to as a switching assembly) that can switch to energize any one or more electrode-pairs among electrodes 50. A sequenced IRE ablation protocol utilizing an embodiment of the disclosed method, such as shown in FIG. 3, is stored in a memory 48 of console 24.

Physician 30 inserts distal end 22a of shaft 22 through a sheath 23 into heart 26 of a patient 28 lying on a table 29. Physician 30 navigates the distal end of shaft 22 to a target location in heart 26 by manipulating shaft 22 using a manipulator 32 near the proximal end of the catheter and/or deflection from the sheath 23. During the insertion of distal end 22a, deflectable tip section 40 is maintained in a straightened and constrained configuration by sheath 23. By containing tip section 40 in a straightened configuration, sheath 23 also serves to minimize vascular trauma along the way to target location.

Once distal end 22a of shaft 22 has reached the target location, physician 30 retracts sheath 23 and deflects tip section 40, and further manipulates shaft 22 to place electrodes 50 disposed over tip section 40 in contact with ostium 51 the pulmonary vein.

Electrodes 50 are connected by wires running through shaft 22 to processor 41 controlling switching box 46 of interface circuits 44 in a console 24.

In an embodiment, processor 41 receives electrical impedance signals, measured between electrodes 50 and surface electrodes 38, which are seen in the exemplified system as attached by wires running through a cable 37 to the chest of patient 28. A method for tracking the positions of electrodes 50 using the measured impedances is implemented in various medical applications, for example in the CARTO™ system, produced by Biosense-Webster (Irvine, California) and is described in detail in U.S. Pat. Nos. 7,756,576, 7,869,865, 7,848,787, and 8,456,182, whose disclosures are all incorporated herein by reference. This method is sometimes called Advanced Catheter Location (ACL). Console 24 drives a display 27, which shows the tracked position and/or shape of deflectable tip section 40 inside heart 26.

As further shown in inset 25, distal end 22a comprises a magnetic position sensor 39 contained within distal end 22a just proximally to tip section 40. During navigation of distal end 22a in heart 26, console 24 receives signals from magnetic sensor 39 in response to magnetic fields from external field generators 36, for example, for the purpose of measuring the position of tip section 40 in the heart and, optionally, presenting the tracked position on a display 27. Magnetic field generators 36 are placed at known positions external to patient 28, e.g., below patient table 29. Console 24 also comprises a driver circuit 34, configured to drive magnetic field generators 36.

The method of position sensing using external magnetic fields is implemented in various medical applications, for example, in the CARTO™ system, produced by Biosense-Webster and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publication Nos. 2002/0065455 A1, 2003/0120150 A1 and 2004/0068178 A1, whose disclosures are all incorporated herein by reference.

Processor 41, shown comprised in control console 24, is typically a general-purpose computer, with suitable front end and interface circuits 44 for receiving signals from catheter 21, as well as for applying RF energy treatment via catheter 21 in a left atrium of heart 26 and for controlling the other components of system 20. Processor 41 typically comprises a software in a memory 48 of system 20, that is programmed to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, included in FIG. 4, that enables processor 41 to perform the disclosed steps, as further described below.

Selecting Sequential Electrodes During IRE

Figure 2:
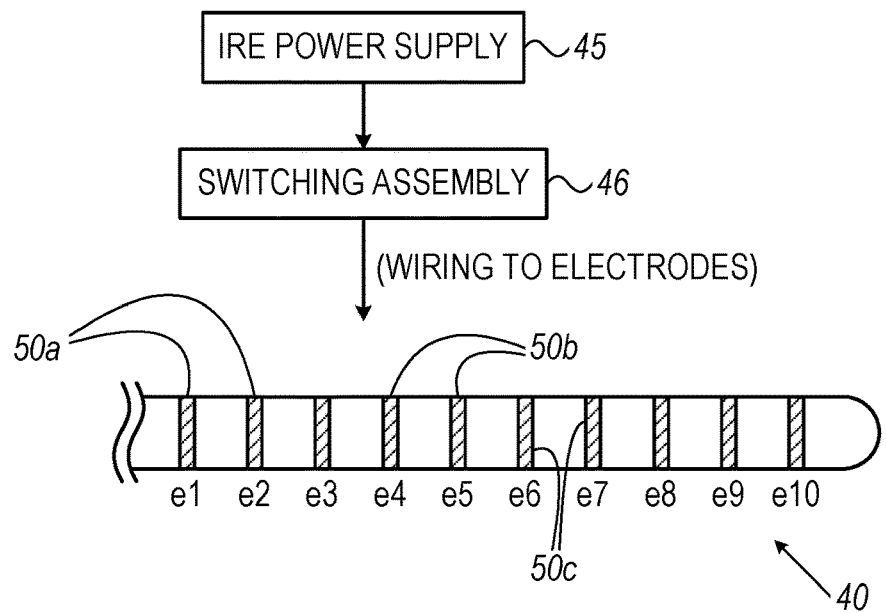
FIG. 2 is a schematic, pictorial side view of the multi-electrode deflectable tip section of the catheter of FIG. 1, in accordance with an exemplary embodiment of the invention.

FIG. 2 is a schematic, pictorial side view of multi-electrode deflectable tip section 40 of catheter 21 of FIG. 1, in accordance with an exemplary embodiment of the invention. Deflectable tip section 40, which is shown straight but can take a bent shape or even a loop shape, has ten electrodes 50 disposed over section 40 and designated e1-e10.

Using switching assembly 46 of system 20, one or more IRE pulses can be delivered from IRE ablation power source 45 of system 20 independently to each electrode-pair selected of the ten electrodes, as prespecified, for example, by an algorithm, such as one schematically illustrated by FIG. 3. In the illustrated exemplary embodiment, electrode-pairs e1-e2 (50a), e4-e5 (50b) and e6-e7 (50c) are selected to be energized to deliver IRE pulses. Thus, rather than activating pairs e1-e2, e2-e3, e3-e4, e4-e5, e5-e6, e6-e7 sequentially where electrodes e2, e3, e4, e5, e6 have electrical current passing with no time to cool in between, the pairs may be sequenced e1-e2, e4-e5, e6-e7, and, subsequently, e2-e3, e5-e6, e3-e4, so that each electrode 50 has time to cool before being used again for IRE ablation. The pairs may be energized sequentially, or groups of electrodes may be energized together (e.g. e1-e2 and e6-e7; e4-e5 and e2-e3; e5-e6 and e3-e4). The above description has assumed that adjacent electrodes are energized. However, electrodes may be paired in other ways, for example e1-e4, e2-e5, e3-e6, e4-e7.

FIG. 3 is a schematic front view of sequenced energization of electrode-pairs of a multi-electrode deflectable tip section 40 of a catheter deployed in a form of a loop 404, in accordance with an exemplary embodiment of the present invention. FIG. 3 may schematically represent a front view of the aforementioned Lasso™ catheter, being deployed at an ostium of a PV.

In FIG. 3, each concentric ring 60 represents a duration, e.g., during a refractory period of a heart cycle, at which selected electrodes are energized to deliver IRE bipolar pulses.

In an embodiment, the pulses are gated to be applied synchronously with the beating of the heart, i.e., to be applied during a refractory period of the tissue. Ventricular and atrial electrograms at ventricular or atrial tissue locations are usually acquired by electrodes in contact with tissue at the location catheter, e.g., during electrophysiological mapping of wall tissue portions of each of the respective cardiac chambers. A ventricular or an atrial refractory period is a duration of a pause in neural activity at the tissue location, after an activation occurred in tissue of either of the above cardiac chambers. Typically, a refractory period largely coincides with the QRST interval portion of a cardiac cycle demonstrated in a ventricular or an atrial electrogram taken at the location. A refractory period can be deliberately induced at a tissue portion of the heart, for example, using a pacing catheter to pace the tissue at the tissue location.

The duration number one to six (e.g., cycle numbers 1, 2, 3, 4, 5, 6) and respective identity of electrode-pairs that are energized thereon during a refractory period of each cycle is listed in Table I below:

TABLE I

Sequenced Electrode Pair Selection

| Cycle # | Electrode-Pairs Energized |
|---|---|
| 1 | e1-e2, e4-e5, e7-e8 |
| 2 | e2-e3, e5-e6, e8-e9 e10-e1 |
| 3 | e3-e4, e6-e7, e9-e10 |
| 4 | e4-e5, e7-e8, e1-e2 |
| 5 | e2-e3, e5-e6, e8-e9 |
| 6 | e3-e4, e6-e7, e9-e10 |

As seen, each electrode is energized four times over the six durations, with a pause every two successive energizations (i.e., pauses 61 of e1, pauses 62 of e2, pauses 63 of e3, pauses 64 of e4, pauses 65 of e5, pauses 66 of e6, pauses 67 of e7, pauses 68 of e8, pauses 69 of e9, pauses 70 of e10).

The dark circular sections (77) represent arc regions of tissue over a circumference of an ostium that received IRE ablation. As seen, the entire ostium was IRE ablated twice during the six-period IRE treatment.

By way of example, the pulse applied at each cycle may be specified by the following Table II:

TABLE II

| Parameter | Value |
|---|---|
| Preset IRE peak voltage | 2000 V |
| Pulse width | 5 microseconds |
| Number of pulses in train | 20 |

The pictorial side view shown in FIG. 3 is chosen by way of example, where other exemplary embodiments are possible. For example, in another embodiment, arc sections 77 are longer, e.g., representing bipolar voltages applied between two next-adjacent electrodes (e.g., every third electrode), such as e1-e3, e2-e4, e3-e5, and so on, that generate partially spatially overlapping electrical fields.

In another exemplary embodiment, no more than a single electrode-pair is activated at any given time. In this case the protocol of Table I can be replaced by a protocol given in table III below, in which each cycle specifies a single electrode pair that is activated alone:

TABLE III

| Cycle # | Electrode-Pair Energized |
|---|---|
| 1 | e1-e2 |
| 2 | e4-e5 |
| 3 | e7-e8 |
| 4 | e2-e3 |
| 5 | e5-e6 |
| 6 | e8-e9 |
| 7 | e10-e1 |
| 8 | e3-e4 |

TABLE III-continued

| Cycle # | Electrode-Pair Energized |
|---|---|
| 9 | e6-e7 |
| 10 | e9-e10 |
| 11 | e4-e5 |
| 12 | e7-e8 |
| 13 | e1-e2 |
| 14 | e2-e3 |
| 15 | e5-e6 |
| 16 | e8-e9 |
| 17 | e3-e4 |
| 18 | e6-e7 |
| 19 | e9-e10 |

In yet another exemplary embodiment, at least some of the bipolar IRE pulses are applied between non-adjacent electrodes. In still another exemplary embodiment, at least some of the bipolar IRE pulses are applied between groups of electrodes shorted together (e.g., between e1,e2,e3 shorted to one another and e6,e7,e8 shorted to one another, or between e1,e2,e3,e4 shorted to one another and e9), as opposed to pairs of individual electrodes such as between e2 and e3.

Figure 4:
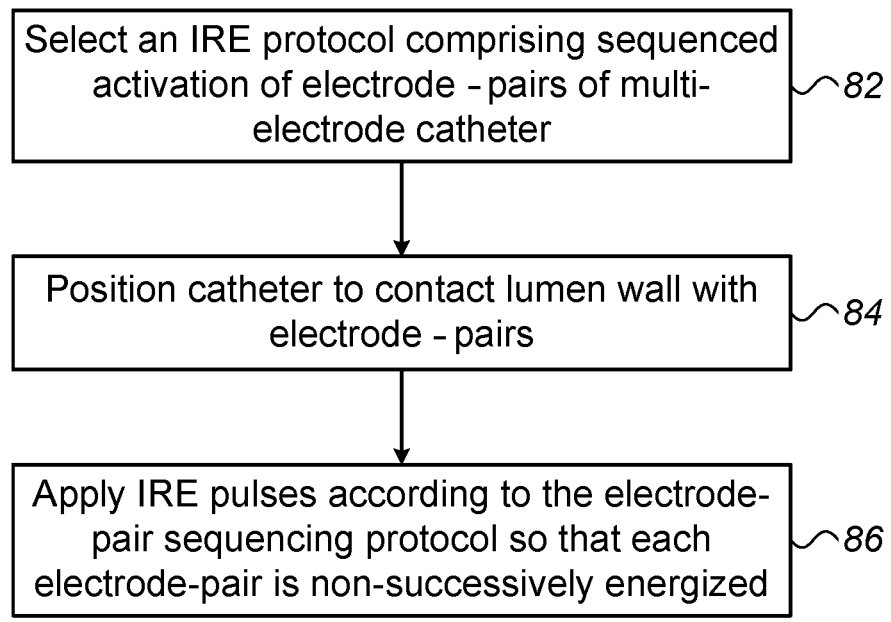
FIG. 4 is a flow chart that schematically illustrates a method for using electrode-pairs of the catheter head of FIG. 2 for sequential irreversible electroporation (IRE) ablation, in accordance with an exemplary embodiment of the invention.

FIG. 4 is a flow chart that schematically illustrates a method for using electrode-pairs of the catheter head of FIG. 2 for sequential irreversible electroporation (IRE) ablation, in accordance with an exemplary embodiment of the present invention. The algorithm, according to the presented exemplary embodiment, carries out a process that begins at an IRE protocol selection step 82, when physician 30 selects an IRE protocol comprising sequenced activation of electrode-pairs of a multi-electrode catheter, such as pairs of electrodes 50 of catheter 21. An example protocol is provided above by Tables I and II.

Next, physician 30 inserts, navigates, and positions the catheter at a target location within a lumen of a patient, such as at ostium 51, at a balloon catheter positioning step 84.

Finally, physician 30 uses system 20, using the IRE protocol, to apply IRE pulses according to the sequence specified in the protocol (e.g., according to the sequence of Table I), to non-successively energize each of the electrode-pairs, at a sequenced IRE ablation step 86.

The example flow chart shown in FIG. 4 is chosen purely for the sake of conceptual clarity. In alternative embodiments, additional steps may be performed, such as processor 41 monitoring measured temperature of electrodes, and acting according to measured temperatures, if required, such as disconnecting an overheated electrode pair from further use in the specified protocol.

Although the embodiments described herein mainly address pulmonary vein isolation, the methods and systems described herein can also be used in other applications that may require a sequenced ablation, such as, for example, in renal denervation, and generally, in ablating other organs, such as in treatment of lung or liver cancers.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

We claim:

1. An irreversible electroporation (IRE) method, comprising:
   placing multiple electrodes of a catheter in contact with tissue of an organ;
   generating bipolar IRE pulses; and
   ablating the tissue by applying the bipolar IRE pulses to pairs of the multiple electrodes, in accordance with an order in which successive activations of a first electrode-pair of the pairs of the multiple electrodes over a same heartbeat cycle or over successive heartbeat cycles are interleaved with activation of at least one other electrode-pair of the pairs of the multiple electrodes such that any successive activations of the first electrode-pair are spaced in time, wherein the first electrode-pair and the at least one other electrode-pair include two electrodes, respectively, of the multiple electrodes and the at least one other electrode-pair excludes any of the two electrodes of the first electrode-pair and wherein interleaving the successive activations of the two electrodes of the first electrode-pair and the two electrodes of the at least one other electrode-pair comprises:
   A) activating only the two electrodes of the first electrode-pair of the multiple electrodes before activating the two electrodes of the at least one other electrode-pair, and
   B) activating one of: i) at least one of the first electrode-pair or the at least one other electrode-pair as a pair of directly adjacent electrodes; ii) next-adjacent pairs of the multiple electrodes, or iii) non-adjacent pairs of the multiple electrodes, wherein the two electrodes in at least one of the pairs of non-adjacent electrodes are separated by at least two intervening electrodes of the multiple electrodes.

2. The method according to claim 1, wherein the first electrode pair and the at least one other electrode pair have a same inter-electrode distance.

3. The method according to claim 1, wherein the tissue comprises cardiac tissue, and wherein applying the bipolar IRE pulses comprises gating the bipolar IRE pulses to synchronize with refractory periods of the cardiac tissue.

4. An irreversible electroporation (IRE) system, comprising:
   a catheter having multiple electrodes that are configured to be placed in contact with a tissue of an organ;
   an IRE ablation power source configured to generate bipolar IRE pulses to ablate the tissue;
   a processor, which is configured to provide instructions to apply the bipolar IRE pulses to pairs of the multiple electrodes, in accordance with an order in which successive activations of a first electrode-pair of the pairs of the multiple electrodes over a same heartbeat cycle or over successive heartbeat cycles are interleaved with activation of at least one other electrode-pair of the pairs of the multiple electrodes such that any successive activations of the first electrode-pair are spaced in time, wherein the first electrode-pair and the at least one other electrode-pair include two electrodes, respectively, of the multiple electrodes and the at least one other electrode-pair excludes any of the two electrodes of the first electrode-pair and wherein interleaving the successive activations of the two electrodes of the first electrode-pair and the two electrodes of the at least one other electrode-pair comprises:
   A) activating only the two electrodes of the first electrode-pair of the multiple electrodes before activating the two electrodes of the at least one other electrode-pair, and
   B) activating one of: i) at least one of the first electrode-pair or the at least one other electrode-pair as a pair of directly adjacent electrodes; ii) next-adjacent pairs of the multiple electrodes, or iii) non-adjacent pairs of the multiple electrodes, wherein the two electrodes in at least one of the pairs of non-adjacent electrodes are separated by at least two intervening electrodes of the multiple electrodes; and
   a switching assembly that is configured to switch the IRE ablation power source between the first electrode-pair and the at least one other electrode, and wherein the processor is configured to apply the bipolar IRE pulses in accordance with the order by controlling the switching assembly.

5. The system according to claim 4, wherein the first electrode-pair and the at least one other electrode-pair have a same inter-electrode distance.

6. The system according to claim 4, wherein the tissue comprises cardiac tissue, and wherein the processor is configured to gate the bipolar IRE pulses to synchronize with refractory periods of the cardiac tissue.

7. A computer program product, comprising a non-transitory computer-readable medium having computer-readable program code embodied therein to be executed by one or more processors, the computer-readable program code including instructions to:
   generate bipolar irreversible electroporation (IRE) pulses; and
   ablate tissue by applying the bipolar IRE pulses to pairs of the multiple electrodes, in accordance with an order in which successive activations of a first electrode-pair of the pairs of the multiple electrodes over a same heartbeat cycle or over successive heartbeat cycles are interleaved with activation of at least one other electrode-pair of the pairs of the multiple electrodes such that any successive activations of the first electrode-pair are spaced in time, wherein the first electrode-pair and the at least one other electrode-pair include two electrodes, respectively, of the multiple electrodes and the at least one other electrode-pair excludes any of the two electrodes of the first electrode-pair and wherein interleaving the successive activations of the two electrodes of the first electrode-pair and the two electrodes of the at least one other electrode-pair comprises:
   A) activating only the two electrodes of the first electrode-pair of the multiple electrodes before activating the two electrodes of the at least one other electrode-pair, and
   B) activating one of: i) at least one of the first electrode-pair or the at least one other electrode-pair as a pair of directly adjacent electrodes; ii) next-adjacent pairs of the multiple electrodes, or iii) non-adjacent pairs of the multiple electrodes, wherein the two electrodes in at least one of the pairs of non-adjacent electrodes are separated by at least two intervening electrodes of the multiple electrodes.

8. The computer program product according to claim 7, wherein the first electrode pair and the at least one other electrode pair have a same inter-electrode distance.

9. The computer program product according to claim 7, wherein the tissue comprises cardiac tissue, and wherein applying the bipolar IRE pulses comprises gating the bipolar IRE pulses to synchronize with refractory periods of the cardiac tissue.

\* \* \* \* \*